(12) United States Patent
Hedén et al.

(10) Patent No.: US 12,357,284 B2
(45) Date of Patent: Jul. 15, 2025

(54) BIOPSY INSTRUMENT

(71) Applicant: Resitu Medical AB, Uppsala (SE)

(72) Inventors: Per Hedén, Stockholm (SE); Per Egnelöv, Uppsala (SE)

(73) Assignee: RESITU MEDICAL AB, Uppsala (SE)

( * ) Notice: Subject to any disclaimer, the term of this patent is extended or adjusted under 35 U.S.C. 154(b) by 0 days.

(21) Appl. No.: 18/852,547

(22) PCT Filed: Mar. 28, 2023

(86) PCT No.: PCT/SE2023/050275
§ 371 (c)(1),
(2) Date: Sep. 30, 2024

(87) PCT Pub. No.: WO2023/195890
PCT Pub. Date: Oct. 12, 2023

(65) Prior Publication Data
US 2025/0099087 A1     Mar. 27, 2025

(30) Foreign Application Priority Data
Apr. 5, 2022 (SE) .................................. 2250433-6

(51) Int. Cl.
*A61B 10/02* (2006.01)
(52) U.S. Cl.
CPC ............................... *A61B 10/0233* (2013.01)
(58) Field of Classification Search
CPC ............. A61B 10/0233; A61B 10/025; A61B 10/0266; A61B 10/04; A61B 2010/0208; A61B 2017/32004
See application file for complete search history.

(56) References Cited

U.S. PATENT DOCUMENTS 5,817,034 A * 10/1998 Milliman ............... A61B 17/34
606/171
6,007,495 A * 12/1999 Matula ............... A61B 10/0266
600/564
(Continued)

FOREIGN PATENT DOCUMENTS

CN     111631810 A     9/2020
EP     0429390 A1     5/1991
(Continued)

OTHER PUBLICATIONS

Swedish Intellectual Property Office, Stockholm, Sweden, Swedish search report, Nov. 1, 2022.
(Continued)

*Primary Examiner* — Devin B Henson
(74) *Attorney, Agent, or Firm* — Noréns Patentbyrå AB

(57) ABSTRACT

A biopsy instrument comprising:
  a first part (1) comprising a cutting tube (4) having a distal cutting edge (12),
  a second part (2) comprising a penetration rod (5),
  a third part (3) comprising a knife (6) arranged centrally along a length of the biopsy instrument, having a radially extending portion (7) at its distal end substantially corresponding to an inner radius of the cutting tube,
  the first and second parts are coaxially arranged around the third part,
  the first part is movable distally from the second part from a retracted position to an extended position,
  the third part is axially movable between a retracted position and an extended position, the third part being rotationally movable in at least the extended position,
  a stop inhibits a rotational movement of the second part
  (Continued)

in relation to the first part or inhibits rotational movement in all axial positions except one or more axial release positions.

12 Claims, 4 Drawing Sheets

(56) References Cited

U.S. PATENT DOCUMENTS

| | | | |
|---|---|---|---|
| 10,973,498 B2* | 4/2021 | Sjunnesson | A61B 10/0275 |
| 2005/0054947 A1 | 3/2005 | Goldenberg | |
| 2006/0030785 A1* | 2/2006 | Field | A61B 10/02 |
| | | | 600/567 |
| 2011/0004120 A1 | 1/2011 | Drubetsky | |

FOREIGN PATENT DOCUMENTS

| | | |
|---|---|---|
| EP | 3200700 A1 | 8/2017 |
| GB | 2237992 A | 5/1991 |

OTHER PUBLICATIONS

Swedish Intellectual Property Office, Stockholm, Sweden, International Search Report, May 4, 2023.

* cited by examiner

BIOPSY INSTRUMENT

The present invention concerns a biopsy instrument.

The majority of biopsy instruments are large, electrically driven and voluminous apparatuses. The aim of the present invention is to provide a handheld and easy to use instrument. An aim is also to support the right use and inhibit faulty use.

According to a first aspect of the present invention a biopsy instrument is provided, comprising:
- a first part comprising a cutting tube having a distal cutting edge,
- a second part comprising a penetration rod,
- a third part comprising a knife arranged centrally along a length of the biopsy instrument, having a radially extending portion at its distal end substantially corresponding to an inner radius of the cutting tube,
- the first and second parts are coaxially arranged around the third part,
- the first part is movable distally from the second part from a first, retracted, position to a second, extended, position,
- the third part is axially movable between a first, retracted, position and a second, extended, position, the third part being rotationally movable in at least the second, extended, position, and
- a stop inhibiting a rotational movement of the second part in relation to the first part or inhibits rotational movement in all axial positions except one or more axial release positions.

According to an embodiment of the biopsy instrument the third part is only rotationally movable relative the first part when the third part is in its second, extended, position. Preferably, the third part is only rotationally movable relative the first part when also the first part is in its second, extended, position. Most preferred, the third part is only rotationally movable relative the first part when the second part remains in its original axial position in relation to the first and third part.

According to an embodiment of the biopsy instrument a second stop inhibits a rotational movement of the second part in relation to the third part. Preferably, the stop is movable with the axial movement of the third part.

According to an embodiment of the biopsy instrument the stop is in a release position only when the third part is in its second, extended, position, and wherein the second part also is released for rotational movement relative the first part. Preferably, the stop cooperates with a transverse slot in the first part when in the release position.

According to an embodiment of the biopsy instrument the third part is rotatable together with the second part.

According to an embodiment of the biopsy instrument the first part will be locked in the second, extended, position by a catch, which is releasable so that the first part may be retracted into the instrument to the first, retracted, position.

According to an embodiment of the biopsy instrument the knife is an electrosurgical knife.

According to an embodiment of the biopsy instrument the cutting tube is exchangeable.

According to an embodiment of the biopsy instrument the first part comprises a distal handle portion and the cutting tube. Preferably, the second part comprises a proximal handle portion and the penetration rod.

According to an embodiment of the biopsy instrument the third part is movable by means of a slider connected to the third part and arranged in a second slot in the second part.

Preferably, the third part is pushable distally by means of the slider and is retractable by means of a spring means.

SHORT DESCRIPTION OF ENCLOSED DRAWINGS

The present invention will now be described in more detail under referral to the accompanying drawings, in which FIG. 1 shows an embodiment of a biopsy instrument of the present invention in an intermediate position.

DETAILED DESCRIPTION OF EMBODIMENTS OF THE INVENTION

Figure 1:
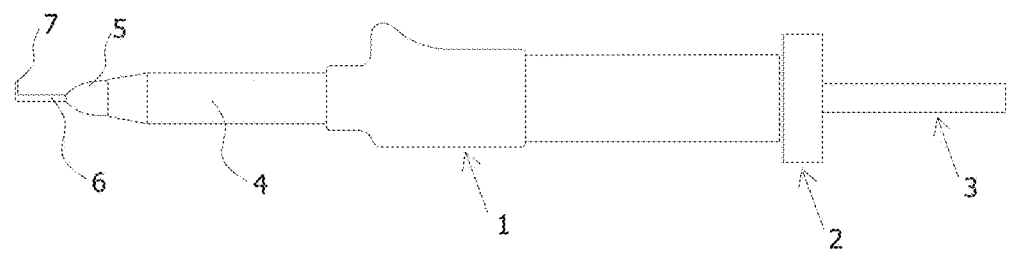

An embodiment of a biopsy instrument of the present invention is shown In FIG. 1. A first part 1 comprising a cutting tube 4 and a second part 2 comprising a penetration rod 5 are shown. Centrally inside, a third part 3 comprising a knife 6, is provided.

Figure 2:
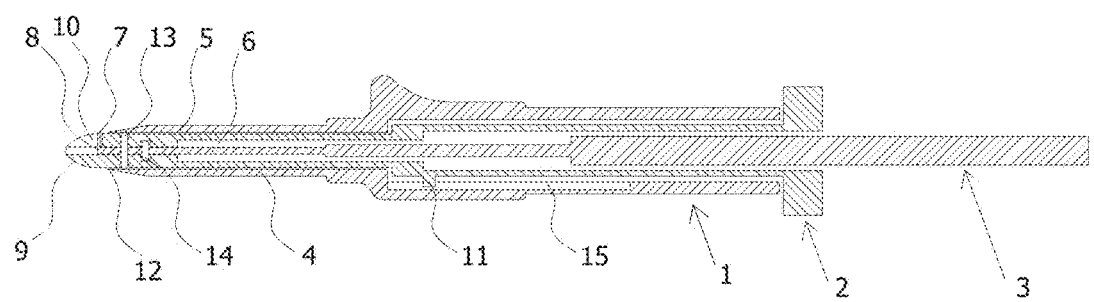
FIG. 2 shows an embodiment of the biopsy instrument of FIG. 1 in a first position in a cut away view.
Figure 4:
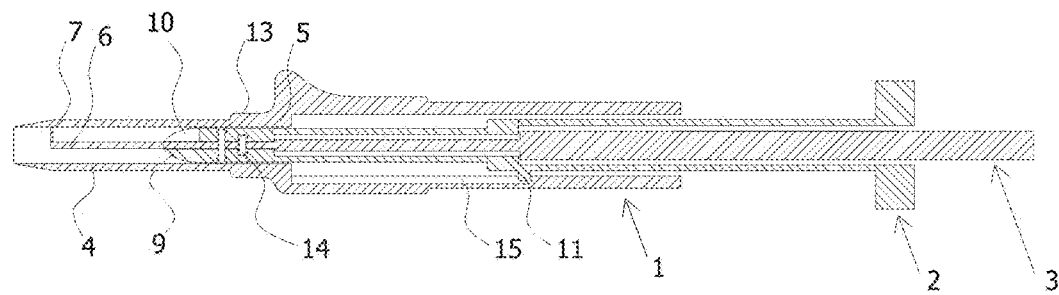
FIG. 4 shows an embodiment of the biopsy instrument of FIG. 1 in a third position in a cut away view.

In FIG. 2 the embodiment of FIG. 1 is shown in a cut away view so that the ingoing parts and their cooperation is seen. Through a central length axis of the instrument the third part 3 comprising a knife 6 is provided. The knife 6 has a radially protruding portion 7 at its distal end 8. The second part 2 coaxially surrounds the third part 3 and its knife 6 and a tip 9 of the penetration rod 5 has a slot 10 in which the radially protruding portion 7 of the knife 6 may rest when the third part 3 is in a first, retracted, axial position, as in FIG. 2. The third part 3 may also be axially moved distally into a second, extended, axial position as shown in FIG. 4.

Figure 3:
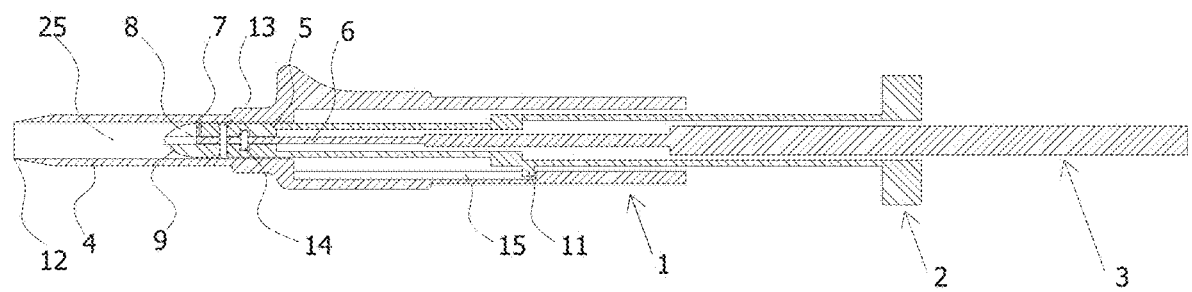
FIG. 3 shows an embodiment of the biopsy instrument of FIG. 1 in a second position in a cut away view.

Also, the first part 1 coaxially surrounds the third part 3. In FIG. 2 the first part 1 is in a first, retracted, axial position. The first part 1 may also be axially moved distally into a second, extended, axial position as shown in FIGS. 3 and 4. The second part 2 remains in its original axial position in relation to the first 1 and third part 3. Obviously, the whole instrument may be moved by a user. A stop 11 inhibits a rotational movement of the second part 2 in relation to the first part 1. The stop 11 may be arranged in for example the second part 2 and the slot 15 may be arranged lengthwise in the first part 1. Obviously, the stop 11 may be arranged in the first part 1 and travels in a slot 15 arranged lengthwise in the second part 2. Anyhow, the stop 11 should not inhibit relative axial movement between the first 1 and the second part 2. It is preferred that a first sealing 13 is provided between cutting tube 4 and the penetration rod 5 in the vicinity of the distal tip 9 thereof. Also, a second sealing 14 may be arranged between the knife 6 and the penetration rod 5 near a distal end of the instrument.

The embodiment of the biopsy instrument according to FIG. 2 may be used in the following way. From start the first 1 and the third part 3 are both in their retracted positions together with the second part 2. The tip 9 of the penetration rod 5 and the encircling cutting tube 4 is pushed into a body from which a target tissue is to be collected. In case any hard tissue is in the way for the instrument it is possible to distally move the third part 3 with its knife 6 in relation to the first 1 and second part 2 so that the knife 6 protrudes out from the slot 10 of the distal end of the instrument, we can call this an intermediate position. Thus, the knife 6 can cut through the hard tissue, if needed.

When the target tissue is reached, the second part 2 and third part 3 are withdrawn so that the first part 1 is axially moved relatively the second part 2 and third part 3 in a distal direction to its second, extended, position, whereby the cutting tube 4 protrudes from the tip 9 of the penetration rod 5 so that it starts cutting and a space 25 is formed in the cutting tube 4 for the target tissue between the cutting edge 12 of the cutting tube 4 and the tip 9 of the penetration rod 5, see FIG. 3. If a first and a second sealings 13, 14 are used an under-pressure is provided in the space 25. It is also conceivable to provide an under-pressure via a tubing through the instrument connected to an under-pressure apparatus. When the cutting edge 12 has passed the target tissue the third part 3 is axially moved distally to its second, extended, position, thereby cutting through the target tissue positioned inside the distal end of the cutting tube 4 with the knife 6, see FIG. 4. While the third part 3 and its knife 6 is in the second, extended, position it is rotated in order to cut off the target tissue from the surrounding tissue.

Thereafter the instrument is withdrawn from the body and then the third part 3 is axially moved to its first, retracted, position. By moving the first part 1 axially towards the first, retracted, position the target tissue inside the cutting tube 4 will be pushed out through a distal end of the cutting tube 4 by means of the penetration rod 5.

Figure 5:
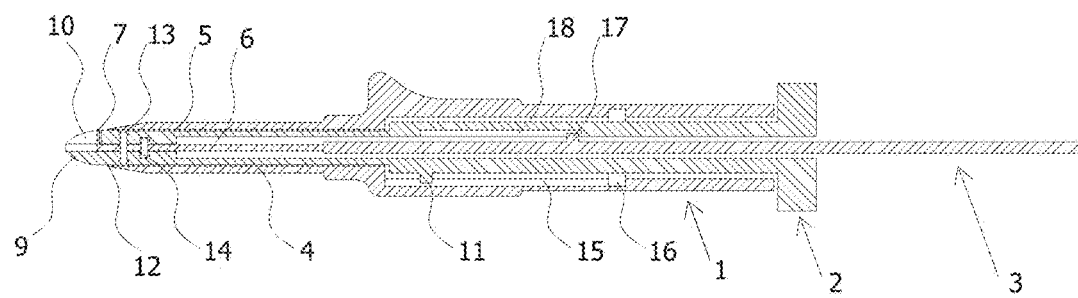
FIG. 5 shows an embodiment of the biopsy instrument in a first position in a cut away view.

According to another embodiment of the biopsy instrument as seen in FIG. 5 the user will be helped by means of further features of the biopsy instrument to handle the biopsy instrument in a correct way.

Figure 6:
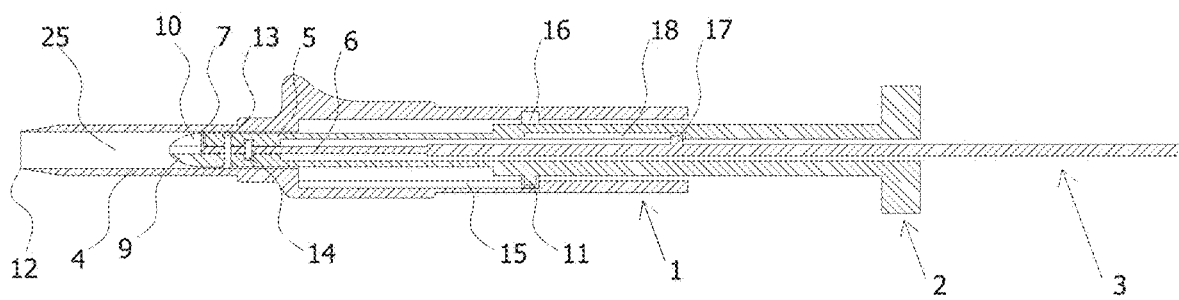
FIG. 6 shows an embodiment of the biopsy instrument of FIG. 5 in a second position in a cut away view.
Figure 7:
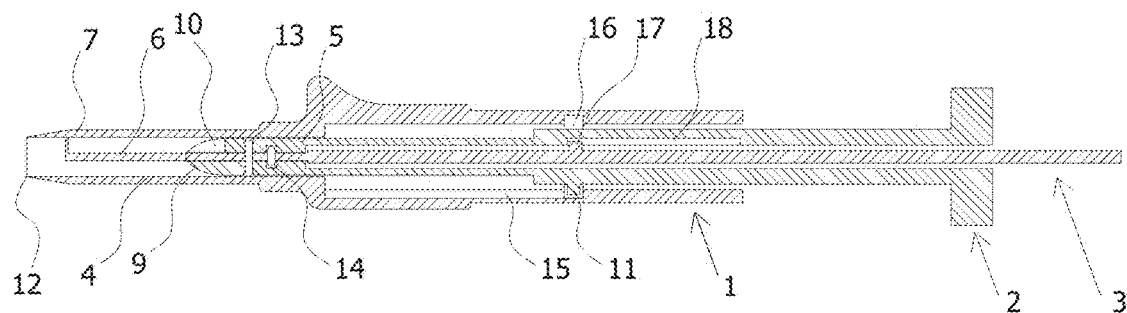
FIG. 7 shows an embodiment of the biopsy instrument of FIG. 5 in a third position in a cut away view.

The embodiment in FIG. 5-7 corresponds to the embodiment of FIG. 1-4 except that the stop 11 may cooperate with a transverse slot 16 arranged in the other part, i.e. if the stop 11 is arranged in the first part 1 the transverse slot 16 is arranged in the second part 2 or, as is shown in FIG. 5-7, the stop 11 is arranged in the second part 2 and the transverse slot 16 is arranged in the first part 1. Additionally, the second 2 and the third part 3 are fixed in the rotational direction. Also, this may be accomplished in a similar way by a second stop 17 sliding lengthwise along a second slot 18. In the shown embodiment the second stop 17 is arranged in the third part 3 and the second slot 18 lengthwise arranged in the second part.

Thus, the first part 1 may be pushed distally, see FIG. 6, whereby the stop 11 slides in the lengthwise slot 15 until it reaches the second, extended, position. In this position the stop 11 is in line with the transverse slot 16 and the second part 2 may rotate relative the first part 1. The second part 2 may bring the third part 3 into cooperating rotation relative the first part 1. When the third part 3 is in its second, extended, position the knife 6 will cut off the target tissue inside the cutting tube 4 during this rotation. The user may more easily rotate the third part 2 by rotating the second part 2.

According to another embodiment of the biopsy instrument as seen in FIGS. 8-12 the user will be helped by means of further features of the biopsy instrument to handle the biopsy instrument in a correct way. For example, it is advantageous that the third part 3 only may rotate in relation to the first part 1 when the first part 1 is in its second, extended, axial position as well as the third part 3 is in its second, extended, axial position.

Figure 8:
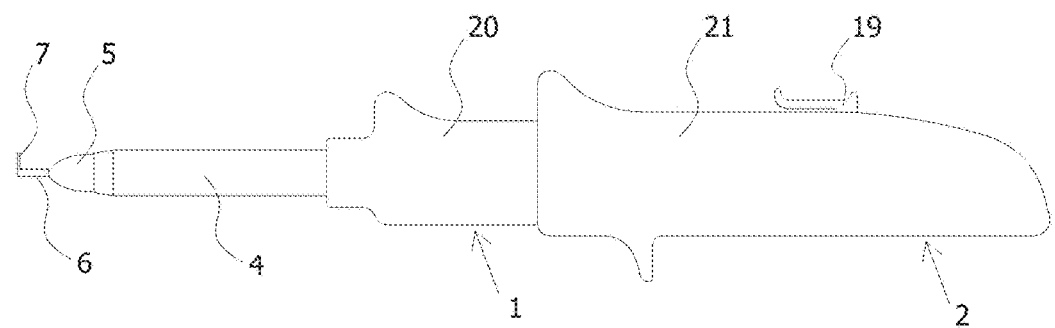
FIG. 8 shows an embodiment of a biopsy instrument of the present invention in an intermediate position.

According to the embodiment of FIGS. 8-12 corresponds to the embodiment of FIGS. 1-4 but has some extra features which will be described below. In FIG. 8 the embodiment of the biopsy instrument is shown in an intermediate position. As also can be seen, this embodiment has more profound handle portions, a distal handle portion 20 and a proximal handle portion 21, and a slider 19.

Figure 9:
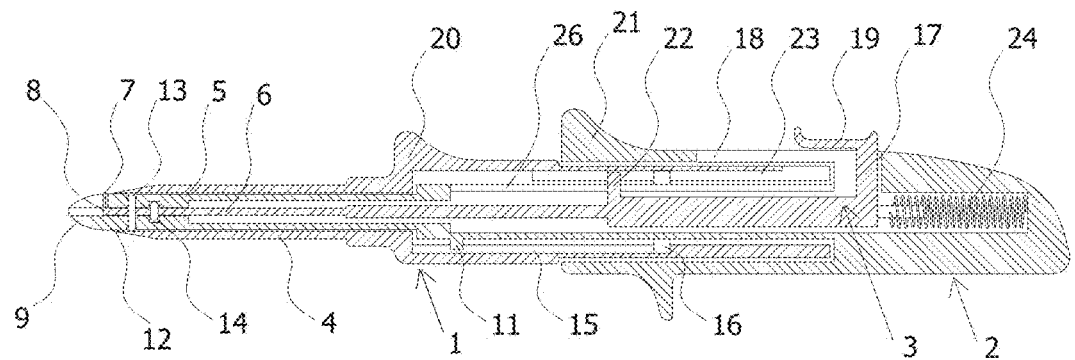
FIG. 9 shows an embodiment of the biopsy instrument of FIG. 8 in a first position in a cut away view.

In FIG. 9 a cut away view of the biopsy instrument is shown. The first part 1 comprises the distal handle portion 20 and the cutting tube 4. The second part 2 comprises the proximal handle portion 21 and the penetration rod 5. The third part 3 comprises the slider 19 and the knife 6.

Figure 12:
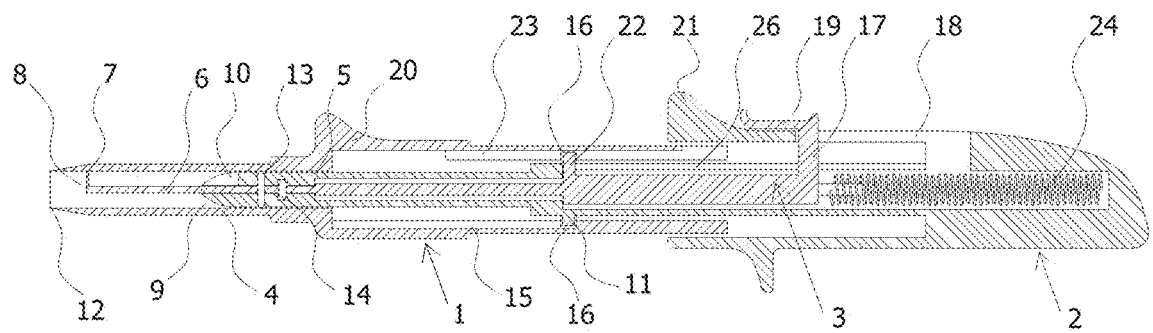
FIG. 12 shows an embodiment of the biopsy instrument of FIG. 8 in a third position in a cut away view.

In this embodiment a stop 11 is arranged at the second part 2 inhibiting rotational movement between the first part 1 and the second part 2 except for when both the first part 1 is in its second, extended, position and the third part 3 is in its second, extended, position and the second part 2 remains in its original, retracted, position. The stop 11 runs in a slot 15 provided in the first part 1. Obviously, the stop 11 and the slot 15 may be arranged vice versa. A transverse slot 16 is arranged in the first part 1 allowing for the stop 11 to be rotationally released when the stop 11 is in line with the transverse slot 16, as is shown in FIG. 12.

In the shown embodiment a second stop 17 is arranged in the third part 3 and a second slot 18 is arranged in the second part, which inhibits rotational movement between the second part 2 and the third part 3. But axial movement is possible as the second stop 17 slides in the second slot 18.

A third stop 22 is arranged in the third part 3 and a third slot 23 is arranged in the first part 1 inhibiting rotational movement between the first part 1 and the third part 3 except for when also the third stop 22 is in line with the transverse slot 16 arranged in the first part 1. Obviously, the third stop 22 and the third slot 23 may be arranged vice versa, at least if the stop 11 is arranged in the first part and the slot 15 is in the third part 3 as well as the transverse slot 16 is arranged in the third part 3. In the shown embodiment the third stop 22 also cooperates with a slot 26 in the second part 2 in order to inhibit rotational movement between the third part 3 and the second part 2. Thus, other designs of the slider 19 can be used without providing a rotational inhibiting function between the third 3 and second part 2.

Figure 10:
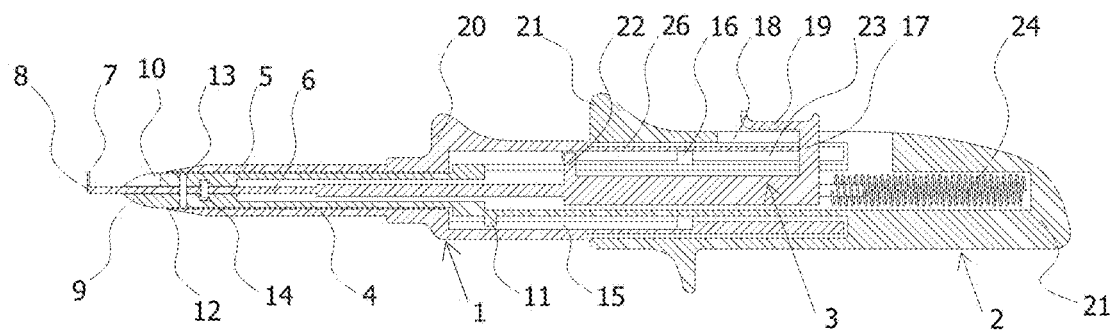
FIG. 10 shows an embodiment of the biopsy instrument of FIG. 8 in an intermediate position in a cut away view.

The slider 19 is connected to the third part 3 and protrudes out of the second part 2 through the second slot 18. By means of the slider 19 the user may move the third part 3 and its knife 6 distally along the length axis of the instrument. In FIG. 10 the slider 19 has been axially moved so that the distal end 8 of the knife 6 having the radially protruding portion 7 is free outside of the instrument. Preferably, a spring 24 is arranged between the third part 3 and the second part 2 in such a way as to retract the third part 3 when a user has pushed the slider 19 distally and then let go of the slider 19.

The embodiment of the biopsy instrument according to FIG. 8-12 may be used in the following way. From start the first 1 and the third part 3 are both in their retracted positions together with the second part 2. The tip 9 of the penetration rod 5 and the encircling cutting tube 4 is pushed into a body from which a target tissue is to be collected. In case any hard tissue is the way for the instrument it is possible to distally move the third part 3 with its knife 6 by means of the slider 19 in relation to the first 1 and second part 2 so that the knife 6 protrudes out from the distal end of the instrument, the intermediate position as shown in FIG. 10. Thus, the knife 6 can cut through the hard tissue, if needed. The spring 24 will bring the third part 19 back to its first, retracted, position. Because of the stop 11 the first 1 and the second part 2 will not rotate relative each other, and because the second stop 17 the third 3 and the second part 2 will not rotate relative each other during this axial movement of the third part 3 relative the first 1 and the second part 2. Thus, a stable axial movement of the third part 3 can be made.

Figure 11:
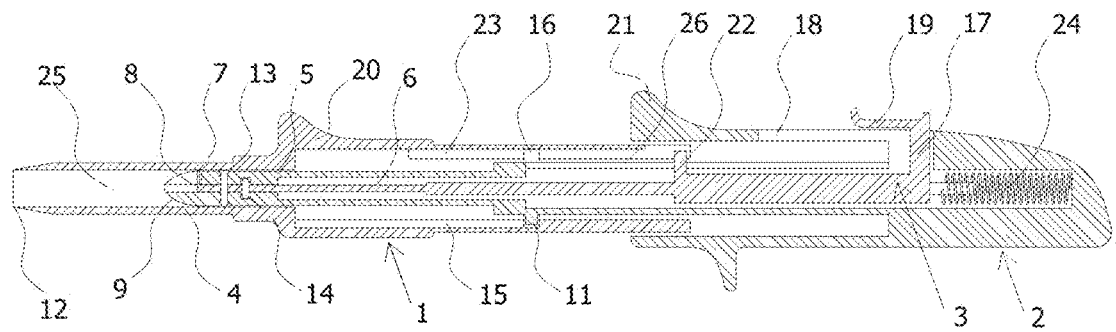
FIG. 11 shows an embodiment of the biopsy instrument of FIG. 8 in a second position in a cut away view.

When the target tissue is reached, the first part 1 is axially moved in a distal direction to its second, extended, position, whereby the cutting tube 4 protrudes from the tip 9 of the penetration rod 5 so that it starts cutting and a space 25 is provided in the cutting tube 4 for the target tissue between the cutting edge 12 of the cutting tube 4 and the tip 9 of the penetration rod 5, see FIG. 11. Due to the stop 11 and the third stop 22 the axial movement will be without any rotational movement. If a first and a second sealings 13, 14 are used an under-pressure is provided in the space 25. It is also conceivable to provide an under-pressure via a tubing through the instrument connected to an under-pressure apparatus. Preferably, a latch latches the first part 1 in its second, extended, position (not shown). The latch is preferably arranged between the first part 1 and the second part 2 and is releasable when the first part 1 is to be retracted.

When the cutting edge 12 has passed the target tissue the third part 3 is axially moved distally to its second, extended, position by means of the slider 19, thereby cutting through the target tissue positioned inside the distal end of the cutting tube 4 with the knife 6, see FIG. 12. While the third part 3 and its knife 6 is in the second, extended, position and also the first part 1 is in its second, extended, position, the second part 2 is rotated in relation to the first part 1, which is possible due to the release position when the stop 11 and the third stop 22 is in line with the transverse slot 16. When the second part 2 is rotated also the third part 3 will be rotated due to the second stop 17 which brings the third part 3 in the rotational movement of the second part 2. The third part 3 is rotated in order to cut off the target tissue from the surrounding tissue. But for a user it is easier to only rotate the second part 2 relative the first part 1 in this step of the method. Preferably, the third part 3 may be latched in its second, extended, position for example by a snap fit between the slider 19 and the second part 2 (not shown). The latch may be released and then the slider 19 and the third part is retracted by the spring 24.

Thereafter the instrument is withdrawn from the body and then the third part 3 is axially pulled back by the spring 24 to its first, retracted, position. By moving the first part 1 axially towards the first, retracted, position the target tissue inside the cutting tube 4 will be pushed out through a distal end of the cutting tube 4 by means of the penetration rod 5.

The knife 6 is preferably an electrosurgical knife using diathermy technology. Although, it is also conceivable to have a mechanical knife, too. Preferably the cutting tube 4 is exchangeable.

The invention claimed is:

1. A biopsy instrument comprising:
    a first part comprising a cutting tube having a distal cutting edge,
    a second part comprising a penetration rod,
    a third part comprising a knife arranged centrally along a length of the biopsy instrument, having a radially extending portion at its distal end substantially corresponding to an inner radius of the cutting tube,
    the first part and the second part are coaxially arranged around the third part,
    the first part is movable distally from the second part from a first, retracted, position to a second, extended, position,
    the third part is axially movable between a first, retracted, position and a second, extended, position, the third part being rotationally movable in at least the second, extended, position, and
    a stop provided on the second part is cooperating with a slot in the first part, or vice versa, thus inhibiting a rotational movement of the second part in relation to the first part in all axial positions except one or more axial release positions wherein the stop in the second part is cooperating with a transverse slot in the first part when in the release position, or vice versa, and additionally a second stop is arranged in the third part cooperating with a second slot lengthwise arranged in the second part, or vice versa, inhibiting a rotational movement of the third part in relation to the second part.

2. The biopsy instrument of claim 1, wherein the third part is only rotationally movable relative the first part when the third part is in its second, ex-tended, position.

3. The biopsy instrument of claim 2, wherein the third part is only rotationally movable relative the first part when also the first part is in its second, ex-tended, position.

4. The biopsy instrument of claim 3, wherein the third part is only rotationally movable relative the first part when the second part remains in its original axial position in relation to the first part and the third part.

5. The biopsy instrument of claim 1, wherein the stop is in a release position only when also the third part is in its second, extended, position, wherein the second part also is released for rotational movement relative the first part.

6. The biopsy instrument of claim 1, wherein the first part will be locked in the second, extended, position by a latch, which is releasable so that the first part may be retracted into the instrument to the first, retracted, position.

7. The biopsy instrument of claim 1, wherein the knife is an electrosurgical knife.

8. The biopsy instrument of claim 1, wherein the cutting tube is exchangeable.

9. The biopsy instrument of claim 1, wherein the first part comprises a distal handle portion and the cutting tube.

10. The biopsy instrument of claim 1, wherein the second part comprises a proximal handle portion and the penetration rod.

11. The biopsy instrument of claim 1, wherein the third part is movable by means of a slider connected to the third part and arranged in the second slot in the second part.

12. The biopsy instrument of claim 11, wherein the third part is pushable distally by means of the slider and is retractable by means of a spring means.

* * * * *